United States Patent
Paige

[19]

[11] Patent Number: 5,982,014
[45] Date of Patent: Nov. 9, 1999

[54] MICROFABRICATED SILICON THERMOPILE SENSOR

[75] Inventor: David F. Paige, Woodland, Calif.

[73] Assignee: Thermalytics, Inc., West Sacramento, Calif.

[21] Appl. No.: 08/850,262

[22] Filed: May 30, 1997

[51] Int. Cl.[6] .......................... H01L 35/04; H01L 35/28; G01N 25/00
[52] U.S. Cl. .............. 257/467; 257/327; 257/9; 257/347; 257/712; 136/225; 136/212; 136/230; 250/338.1; 250/338.4; 250/332; 250/349
[58] Field of Search .................. 257/467, 327, 257/9, 347, 712; 136/225, 212, 224, 230; 250/338.1, 338.4, 332, 349

[56] References Cited

U.S. PATENT DOCUMENTS

| | | | |
|---|---|---|---|
| 3,071,495 | 1/1963 | Hanlein | 117/212 |
| 3,267,727 | 8/1966 | Benzinger | 73/190 |
| 4,111,717 | 9/1978 | Baxter | 136/225 |
| 4,343,960 | 8/1982 | Eguchi et al. | 136/225 |
| 4,558,342 | 12/1985 | Sclar | 257/460 |
| 4,935,345 | 6/1990 | Guilbeau et al. | 435/14 |
| 5,059,543 | 10/1991 | Wise et al. | 257/930 |
| 5,087,312 | 2/1992 | Gerber et al. | 136/225 |
| 5,237,867 | 8/1993 | Cook, Jr. | 73/204.15 |
| 5,251,980 | 10/1993 | Hiraoka et al. | 374/7 |
| 5,343,064 | 8/1994 | Spangler et al. | 257/350 |
| 5,393,351 | 2/1995 | Kinard et al. | 136/225 |
| 5,434,744 | 7/1995 | Fritz et al. | 257/930 |
| 5,451,371 | 9/1995 | Zanini-Fisher et al. | 422/51 |
| 5,634,718 | 6/1997 | Martinis et al. | 374/32 |

OTHER PUBLICATIONS

Integrated Thermopile Sensors in Sensors and Actuators, A21–A23 (1989) 621–630.

*Primary Examiner*—Alexander Oscar Williams
*Attorney, Agent, or Firm*—James M. Ritchey

[57] ABSTRACT

A microfabricated thermopile optimized as a differential temperature sensor provides differential temperature sensing between opposite edges of the device. A plurality of the thermopile sensors are stacked to increase the number of couples possible with an attendant increase in sensitivity.

7 Claims, 4 Drawing Sheets

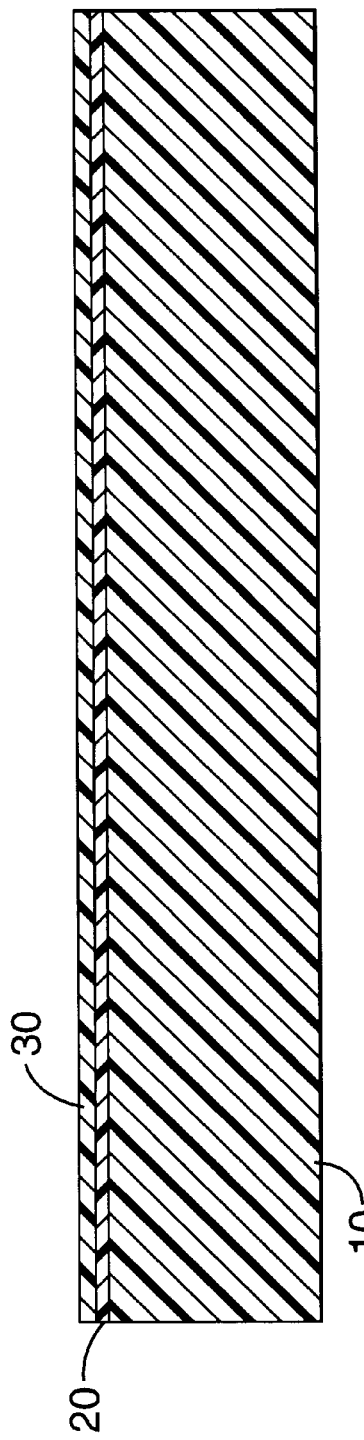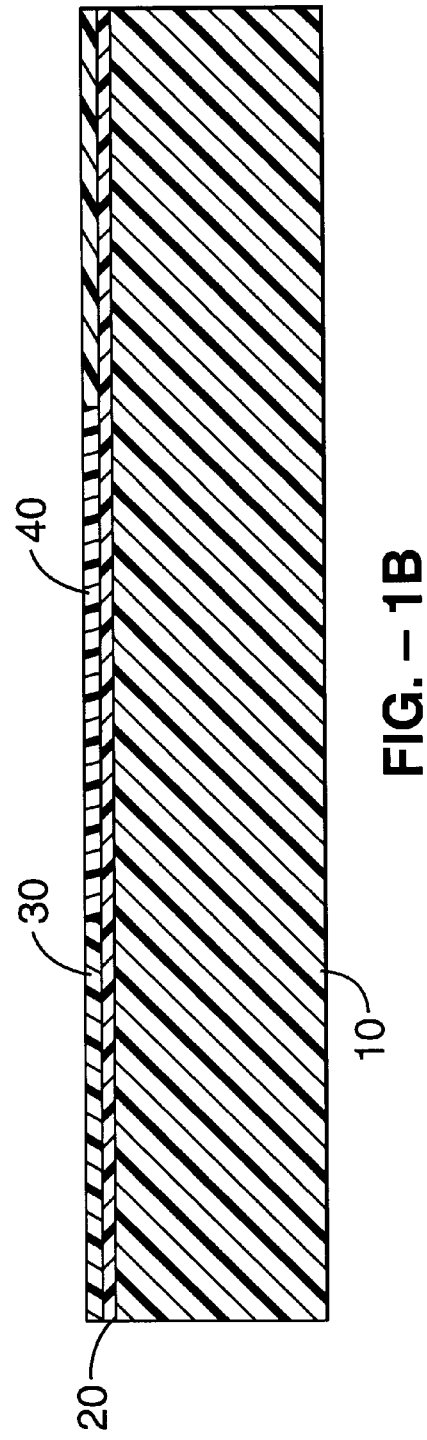

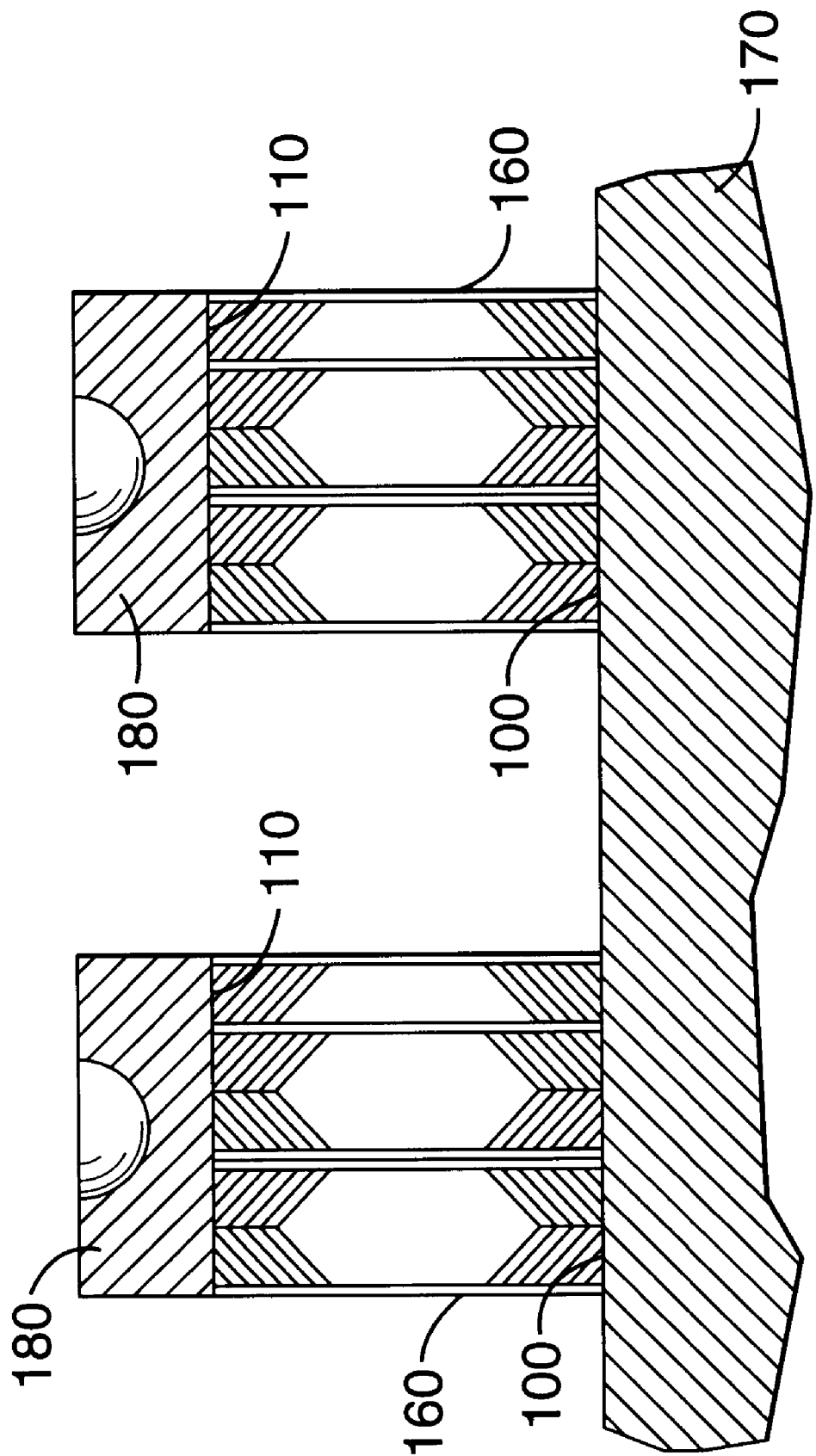

MICROFABRICATED SILICON THERMOPILE SENSOR

BACKGROUND OF THE INVENTION

1. Field of the Invention

A sensor for detecting small changes in temperature for any differential temperature measurement application is disclosed. Specifically, a microfabricated thermopile is optimized as a differential temperature sensor. More specifically, an improved thermopile sensor for microcalorimetric applications is fabricated from silicon that is capable of resolving a $10^{-6}$° C. change with a range of background temperatures between about −50° C. and 100° C.

2. Description of the Background Art

Calorimetry is a powerful and versatile analytical tool because nearly all physical and chemical changes involve the evolution or absorption of heat. However, the high cost of presently available calorimeters, and their relatively low sample throughput, have prevented calorimetry from taking its place as an alternative to analytical methods presently used which are often slower or otherwise less satisfactory. One limiting factor in producing a viable and low cost calorimeter has been the inadequacy of sensors for detecting changes in temperature between a sample and a reference. The subject invention overcomes this and related problems.

A pair of junctions of dissimilar electrically conducting materials, where one is held at a higher temperature than the other, produces a measurable voltage. This phenomenon, observed in semiconductors and metals, was described by Seebeck at the end of the 19th century. With semiconductor couples, the voltage depends on the dopant concentration, which also affects the resistivity of the semiconductor. For a silicon p-n thermocouple junction with resistivity of 0.01 Ωcm for both n and p-types, the Seebeck coefficient, $\Delta V/\Delta T$, is approximately 500 $\mu V/°C$. By connecting hot and cold couples together in a serial fashion, one can increase the voltage output in an additive manner. If 500 pairs of couples are connected in series, they would therefore produce about 250 mV/°C., or about 250 nV/$10^{-6}$° C., which is sufficient for the needs of calorimetry. For 500 couple pairs, the resistance of each arm must be less than 1,000 ohm in order to keep the total sensor resistance below 1 megohm. A higher resistance would increase measurement noise to undesirable levels and place unusual impedance requirements on the voltage measurement device. These considerations constrain the dimensions and the doping of the individual silicon couples. The calorimeter sample cell size and thermal conductivity requirements set dimensional limits for the total sensor size.

A number of researchers have reported microfabricated thermopiles for purposes other than calorimetry, using single crystal silicon or doped poly crystalline silicon, and supported on thinned silicon substrates (Moser and Baltes, 1993, van Herwarrden et al., 1989) or on quartz (Kiely et al., 1994), or using other materials such as aluminum or gallium arsenide or gallium aluminum arsenide. However, in these reports, there are typically tens of couples with hot to cold separations of around a hundred microns, whereas the subject device incorporates a hundred or more couples with a total sensing separation of millimeters.

In heat conduction calorimetry, a differential temperature sensor measures the temperature difference between the sample container at thermal equilibrium (due to the sample's evolution or absorbance of heat) and the reference heat sink. The sensor signal is proportional to the sample's heat rate. However simple in theory, practical implementations are sophisticated and expensive instruments. The thermal resistance of the connection of the sample cell to the heat sink is necessarily kept low, on the order of 1 watt/degree C., which yields a temperature difference of approximately $10^{-6}$° C. for each microwatt of heat flux. A higher thermal resistance may be employed, thus providing a larger temperature difference, but the increased signal results in longer equilibration times (Spink and Wadso, 1976). Even with low thermal resistance, the major limiting factor in the rapid measurement of heat rate is the time required for the sample and its container to reach thermal steady state within the instrument. This requires a minimum of fifteen to sixty minutes, depending on the measurement sensitivity, the system thermal dynamics, and the heat capacity and conductivity of sample and container. Since meaningful measurements cannot be acquired before steady state is approached, sample throughput for each cell is severely limited. Significantly higher processing rates can only be achieved by employing multiple sample stations; therefore the cost per station must be kept low if affordable multi-sample instruments are to be produced.

One common current design element that contributes to the high cost of modern, sensitive calorimeters and thus impedes the production of affordable high throughput instruments is the need for expensive or low sensitivity sensors. As indicated above, thermopiles are the thermal sensor of choice, since they are self exciting and therefore introduce no heat into the measurement system. However, instrument manufacturers currently must choose either commercially available Peltier modules intended for cooling applications and having relatively few junctions, or custom constructed arrays of many thermocouple junctions that are prohibitively expensive. A typical microcalorimeter employing a Peltier module with 10 to 100 bismuth-telluride couples would generate only 2 to 20 nanovolts per microwaft of heat rate and thus require special circuitry for reliable measurement. Even this sensor is relatively expensive. Where several sample cells are desired, each must have its own amplifier, since solid state multiplexers cannot be effectively used at these low signal levels.

There have been many reports and patents describing the construction of a variety of thermopiles, including sensors microfabricated from polycrystalline or single crystal silicon. However, all of these reports concern devices created with a sensing area contained within the plane of the sensor surface, with the output proportional to the temperature difference between this area and an adjoining reference area.

Additionally, U.S. Pat. No. 3,071,495 discloses a method of manufacturing a Peltier thermopile. The method comprises a system for vapor-depositing substances to generate the thermopile.

A thermopile, radiometer, and method for producing same are related in U.S. Pat. No. 3,267,727. Quantitative analysis of 2π and 4π radiant environments is accomplished by producing a thermopile panel having a matrix of thermoelectric junctions.

Described in U.S. Pat. No. 4,111,717 is a thermopile utilized in radiation pyrometry. Thermopile leads are evaporated onto a thin substrate together with a pattern distribution of thermocouple junctions. Included are relatively large reflective areas associated with the region of the thermopile where the cold junctions are located.

U.S. Pat. No. 4,343,960 communicates a thermopile and manufacturing process. Plating and photo-etching techniques are employed to produce a thermopile having segments of one metal and segments of another metal, and the segments of different metals are connected to one another alternately so that the thermocouples are arranged in series on a heat-resistant electrically non-conductive substrate. Each segment has a portion plated on one surface of the substrate and a portion plated on the inner wall of through holes formed in the substrate to connect the two portions plated on the two surfaces of the substrate with each other.

A fully integrated single-crystal silicon-on-insulator process, sensors and circuits are disclosed in U.S. Pat. No. 5,343,064. A layered system is related that includes all of the required components for sensors like capacitive accelerometers and pressure devices.

U.S. Pat. No. 5,059,543 presents a method of manufacturing a thermopile infrared detector. A doped semiconductor supporting rim supports a series of polycrystalline silicon and metal thermocouples. The fully doped semiconductor area serves as an etch stop for a single-sided etch which eliminates the need for front-to-back alignment of the device.

U.S. Pat. No. 5,434,744 reports a method of manufacturing a thermoelectric module that has reduced spacing between semiconductor elements. Alternating bars of thermoelectric materials are arranged between two electrically conductive patterns on two opposing substrates.

A high-sensitivity, silicon-based, microcalorimetric gas sensor is characterized in U.S. Pat. No. 5,451,371. A gas particle sensor for an internal combustion engine includes a pair of polysilicon plates, each plate supporting a pair of resistors, one serving as a heater and the other as a thermometer, one plate being coated with a catalyst to promote combustion of unburned combustible gas constituents.

For the subject invention, a microfabricated thermopile is optimized as a differential temperature sensor. Heat conduction calorimetry is based on the measurement of the temperature difference between a sample container and a stable thermal reference. The subject sensor provides increased sensitivity over the prior art at a lower cost than present sensors, thus allowing the more economical manufacture of such items as a multiple channel calorimeter and in other differential temperature measurement applications. Also, the increased sensitivity of the subject sensor over the prior art permits the use of off-the-shelf data acquisition hardware, further lowering the cost of design and manufacture for instruments utilizing the sensor.

The foregoing patents reflect the state of the art of which the applicant is aware and are tendered with the view toward discharging applicant's acknowledged duty of candor in disclosing information which may be pertinent in the examination of this application. It is respectfully submitted, however, that none of these patents teach or render obvious, singly or when considered in combination, applicant's claimed invention.

SUMMARY OF THE INVENTION

An object of the present invention is to provide a thermopile that is optimized as a differential temperature sensor.

Another object of the present invention is to disclose a thermopile sensor for detecting temperature differences between opposing edges and not traditional planar surfaces.

A further object of the present invention is to describe a relatively inexpensive thermopile sensor.

Still another object of the present invention is to present a thermopile sensor that may be utilized in groups to provide enhanced sensitivity in the detection of temperature differences.

Yet a further object of the present invention is to relate a microfabricated thermopile sensor that may be utilized singularly or in groups to provide enhanced sensitivity in the detection of temperature differences within small spaces.

Disclosed is a thermopile sensor for measuring differential temperatures. Comprising the subject device is a base layer that has a reference heat sink, a sensing heat sink, and an etched area separating the reference and the sensing heat sinks. There is an electrically insulating layer on the base layer that spans the etched area. In the preferred fabrication route, a plurality of alternating p-type and n-type thermopile arms are formed in an electrically conducting layer on the electrically insulating layer. The plurality of arms spans the etched area. The alternating p-type and n-type thermopile arms have an electrical connection between each alternating pair of the p-type and n-type thermopile arms. A thermal reference edge is found above the reference heat sink and a thermal sensing edge above the sensing heat sink. Commonly, the p-type thermopile arms contain a boron dopant and the n-type thermopile arms contain a phosphorus dopant.

Additionally, disclosed is a method of producing the thermopile sensor. The method comprises the steps of: 1) preparing masks for diffusion, etching, and aluminum depositions; 2) diffusing p-type dopant to form p-type thermopile arms into an electrically conductive layer; 3) diffusing n-type dopant to form n-type thermopile arms into the electrically conductive layer; 4) etching the electrically conductive layer to release the n-type and p-type thermopile arms onto an electrically insulating layer; 5) patterning evaporated aluminum connections between the n-type and p-type arms; 6) etching an area on a rear side of a base layer beneath the electrically insulating layer to define heat sink structures; and 6) establishing thermal insulation between the heat sink structures. Generally, the thermal insulation establishing step comprises filling the etched area between heat sink structures with a thermally non-conductive material or bonding the base layer to a thin support. Usually additional steps of separating the individual thermopiles and wiring and potting the individual thermopiles is included in the preferred method.

Other objects, advantages, and novel features of the present invention will become apparent from the detailed description that follows, when considered in conjunction with the associated drawings.

BRIEF DESCRIPTION OF THE DRAWINGS

FIGS. 1A–D are side views of the various steps in the fabrication process for generating the subject thermopile.

FIG. 3 is a side view of a plurality of subject thermopile sensors aligned in sets beneath sample wells in a calorimeter.

DESCRIPTION OF THE PREFERRED EMBODIMENT

Referring now to FIGS. 1A–D, 2, and 3, there is shown a preferred embodiment of an improved thermopile sensor for heat conduction calorimetry and similar differential temperature sensing instruments. Silicon was chosen as the construction material because of its ready commercial availability in a form that makes use of standardized modern microcircuit fabrication facilities. Other equivalent, now known or later developed, materials may be utilized in place of the silicon in the fabrication process.

As presented above, the subject sensor was constructed to provide differential temperature sensing between opposite edges of the device and not the planar surfaces as is standard in the prior art. This configuration lends itself to use as the sensor in a variety of situations, and enables the stacking of multiple devices to increase the number of couples possible with attendant increase in sensitivity (see FIG. 3).

FIGS. 1A–1D and 2 illustrate the sensor fabrication process for an embodiment of the subject thermopile sensor and the final product sensor. It is understood that the described method of fabrication may be altered within standard variations that would be utilized by those skilled in the art and still be within the realm of this disclosure. Usually, the starting material is silicon-on-insulator (SOI) (generally about 6 to 10$\mu$ thick [100] oriented SOI) as obtained from numerous standard semiconductor wafer suppliers.

Generally, the process steps are as follows:
1. Prepare masks for diffusion patterns, etching, and aluminum deposition.
2. Diffuse boron dopant to form the p-type thermopile arms.
3. Diffuse phosphorous to form the n-type arms.
4. Etch 6 micron 100 silicon to release thermopile arms onto the electrically insulating [100] oriented $SiO_2$ layer.
5. Pattern the evaporated aluminum connections between the n and p arms.
6. Etch the rear side to define heat sink structures.
7. Fill the etched area between the heat sinks with a thermally non-conductive material, or bond the wafer to a thin substrate.
8. Saw apart the individual thermopiles.
9. Perform wire bonding and potting operations.

Specifically, FIG. 1A depicts the exemplary starting material of [100] silicon SOI (n-type) as having typical base dimensions of about 3 mm by 500$\mu$ with added layers of about 0.5$\mu$ of silicon dioxide ($SiO_2$) 20 and about 6$\mu$ of 100 silicon 30. Clearly, other equivalent dimensions and substances are within the purview of this disclosure.

Figure 1C:
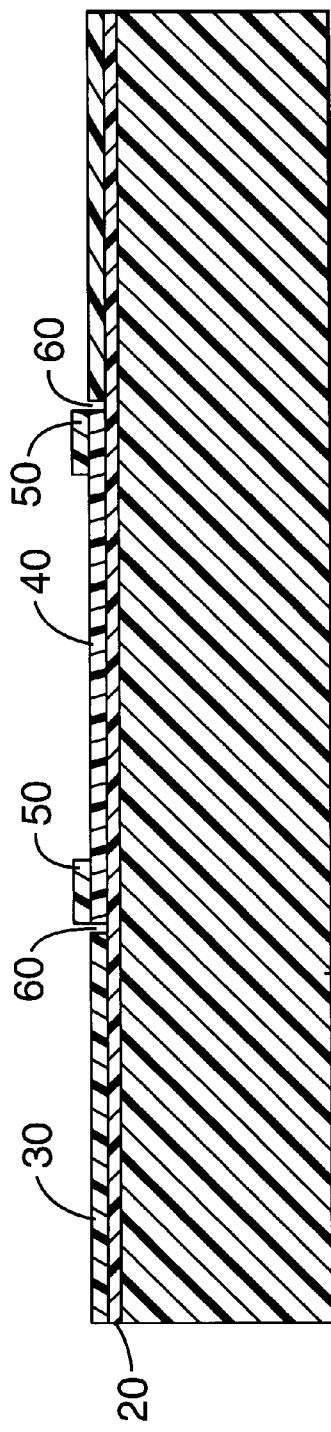
Figure 2:
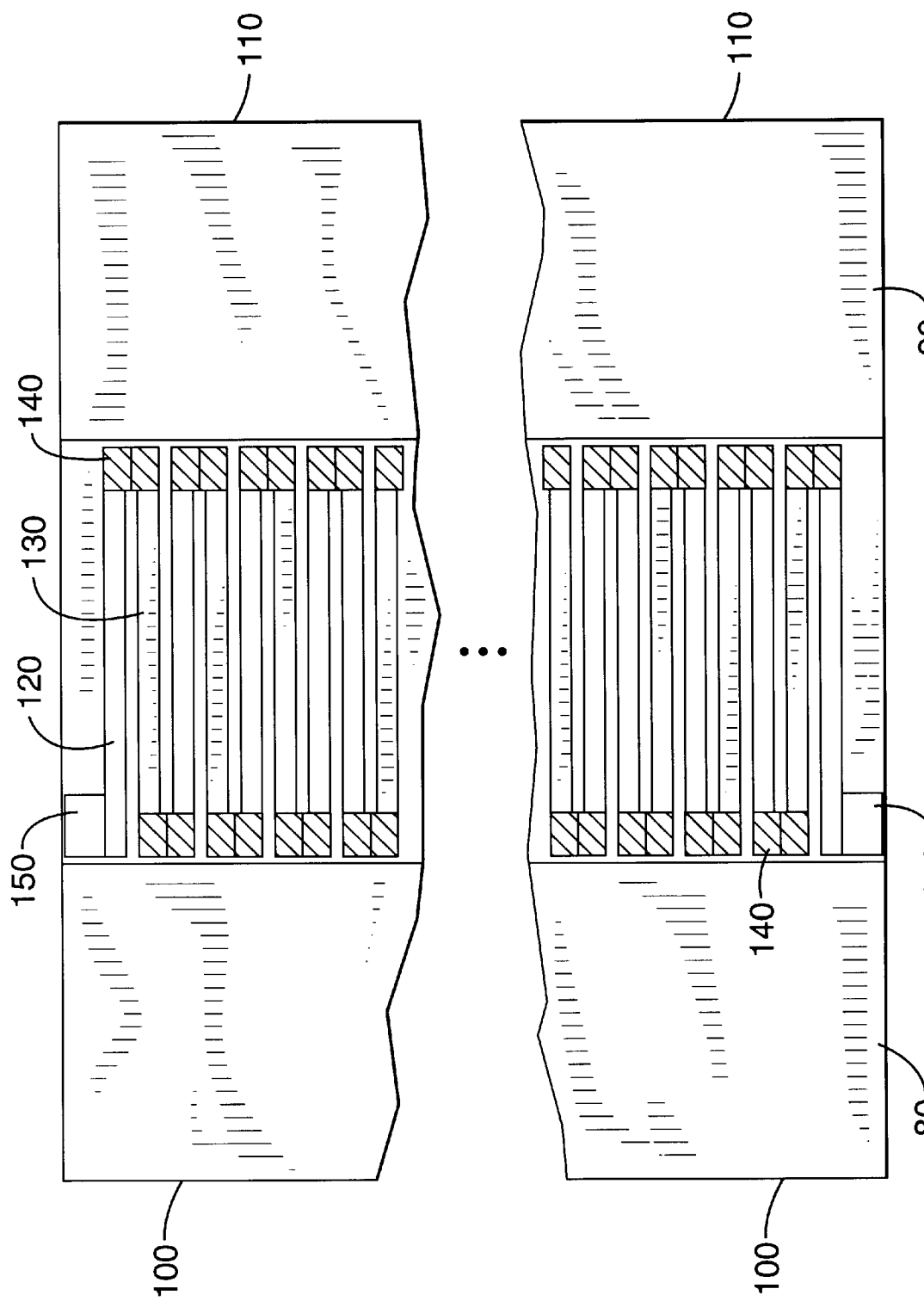
FIG. 2 is top view of the subject thermopile sensor.

FIG. 1B shows the result of the diffusion of appropriate p and n dopants through the mask to define the thermopile arms 40 (see specifically FIG. 2 for p-type arms 120 and n-type arms 130).

FIG. 1C depicts the result of etching 60 the top silicon layer to generate or release the p and n arms 40. Additionally, the patterned application of aluminum p-n junctions 50 is seen in FIG. 1C.

Figure 1D:
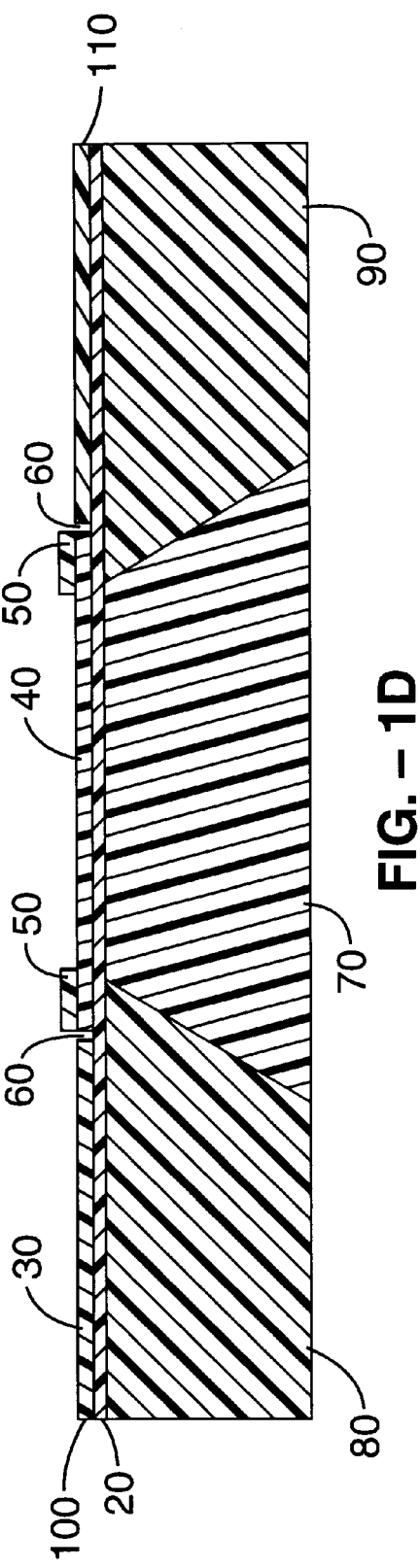

FIG. 1D displays the rear side etching and thermally non-conductive fill area 70 that produces the two opposing heat sinks 80 and 90. Heat sink 80 is a reference heat sink with a reference edge 100. Heat sink 90 is a sensing heat sink with a sensing edge 110.

FIG. 2 shows the upper surface of the generated thermopile sensor. The exact number of paired n-p arms is a function of the selected size of the original starting SIO. Individual thermopiles are created by separating the fabrication into pieces with any desired number of n-p arms per piece. Wire bonding pads 150 are applied to the upper surface of each individual thermopile to facilitate connections to outside interfacing means.

The completed subject sensor functions as follows. The aluminized connections 140 between the n 130 and p 120 doped arms form two rows of thermocouple junctions, one about one-third of the sensor width from the reference edge 100 and the other one-third of the width from the sensing edge 110. The area 70 directly under these arms may be filled with a material having low thermal conductivity (about 0.1 W $m^1K^{-1}$). Beginning just under each row of junctions 140 and extending to the respective reference 100 and sensing 110 edges are the about 0.5 mm thick silicon metal heat sinks 80 and 90 having very high thermal conductivity (about 145 W $m^{-1}K^{-1}$). (The intervening $SiO_2$ (about 1.4 W $m^{-1}K^{-1}$) layer 20 has negligible thermal effect due to its small (about 0.5$\mu$) thickness and the relatively large area of overlap of the arms over the heat sinks.) These heat sinks 80 and 90 act as heat conductors to provide an isothermal region along each edge 100 and 110, respectfully, one at the temperature of the reference 80 and the other at the sample temperature 90. The thermocouple arms 120 and 130 stretch between these areas 80 and 90, but despite also being formed from silicon, their overall thermal conductivity is low because they are thin (on the order of about 6$\mu$ thick, about 10$\mu$ wide, and about 1 mm long).

For exemplary purposes only, a microcalorimeter can employ the subject sensors for detection of heat changes (see co-pending U.S. application Ser. No. 08/792,960 for a microcalorimeter that utilized the subject sensors). Utilization of the subject sensors in a typical calorimeter setting are seen in FIG. 3. In practice, the thermopile sensors may be encapsulated in potting plastic to form a thermopile assembly 160 (see FIG. 3) with the sensor edges 100 and 110 exposed at the faces of the assembly. Usually, the thermopile assemblies 160 will have its lower face bonded to an aluminum thermal reference 170 and its upper face bonded to a sample-containing well 180. For example, one embodiment of the subject sensor assembly has a thermal conductivity of about 1 W/°C., which was chosen to produce a sample temperature change on the order of about $10^{-6°}$ C. per $\mu$watt of sample heat. The completed thermopile exhibits an output voltage proportional to the temperature difference between the two faces of the assembly (i.e., between the thermal reference 170 and the sample well 180). The output sensitivity is projected to be about 125 mV per degree of difference per sensor chip. For two chips back-to-back per sensor (more can be added if desired), a yield of about 250 mV per degree occurs. This compares to a maximum of about 13 mV per degree for presently available bismuth-telluride thermopiles of comparable size. In addition, microfabricated mass production assures a sensor cost well below sensors now used. These differences become especially important for the construction of multiple well calorimeters.

Several variations to enhance the characteristics of the subject thermopile for particular applications include:
1. A different number of couples per chip.
2. Other thermocouple materials, e.g., AlGaAs, which has a lower thermal conductivity than silicon.
3. Different concentrations of n and p dopants, or the use of alternative dopants.
4. A different method of applying dopants, e.g., diffusion vs. ion implantation.
5. Deposition of thin films of thermocouple materials on a substrate of low thermal conductivity.
6. Changing the dimensions of the individual thermopile arms.
7. Changing the dimensions of the isothermal silicon heat sink areas.
8. Use of [100] oriented silicon, which etches faster vertically than horizontally, thus producing more perpendicular edges, and allowing more closely spaced arms.
9. Use of a silicon nitride etch stop layer, with higher thermal conductivity than $SiO_2$ (but more expensive).

It should be remembered and stressed that the subject thermopile has been designed to sense the temperature difference between one edge of the device and the opposite edge. This allows the sensor to be placed on edge perpendicular to, and between, two surfaces to measure their temperature difference. This design also allows the stacking of multiple devices to increase sensitivity or cover a larger area.

Further, it is noted that the starting material with its about 0.5 micron $SiO_2$ layer provides an etch-limiting barrier that enables complete release of the thermopile arms on the front side without being affected by the about 500 micron etch that forms the heat sink structures on the rear side. Also, the aluminum deposition provides ohmic contact between alternating n and p doped arms to eliminate the diode junctions. Thus the only factors affecting the impedance of the device are the dimensions of the arms and the dopant concentration. Additionally, the polyimide fill on the rear side strengthens the structure.

There are additional applications over use in a calorimeter for the subject thermopile sensor. A number of thermopile designs have previously been developed for specific sensing tasks, such as infra-red and visible light sensors, laser power meters (Dehe, et al, 1994), and enzyme activity (Bataillard, et al, 1993). The subject sensor has been designed to measure small differences in temperature between two surfaces. Many uses exist due to its extreme sensitivity and low cost. For example, these thermopiles may be utilized for measuring in situ rates of bioremediation in contaminated soils. Other applications could involve its use in a high sensitivity heat flux plate or a differential temperature sensor.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

REFERENCES

Bataillard, P.; Steffgen, E; Haemmerli, S; Manz A; and others. An integrated silicon thermopile as biosensor for the thermal monitoring of glucose, urea, and penicillin. Biosensors & Bioelectronics, 1993, V8 N2:89–98.

Dehe, A.; Fricke, K.; Hartnagel, H. L. Infrared thermopile sensor based on AlGaAs-GaAs micromachining. (EUROSENSORS VIII, Toulouse, France, Sep. 25–28, 1994). Sensors and Actuators A (Physical), March–April 1995, vol.A47, (no.1–3):432–6.

Kiely, J. H., D. V. Morgan and D. M. Rowe, "The design and fabrication of a miniature thermoelectric generator using MOS processing techniques", Meas. Sci. Technol., 5 (1994) 182–189.

Moser, D. and H. Baltes, "A high sensitivity CMOS gas flow sensor on a thin dielectric membrane", Sensors and Actuators A, 37–38 (1993) 33–37.

Spink, H., and I. Wadso, Calorimetry as an Analytical Tool in Biochemistry and Biology. Methods of Biochemical Analysis, ed. D. Glick, vol. 23, p. 1–159.

van Herwaarden, A. W., D. C. van Duyn, B. W. van Oudheusden and P. M. Sarro, Integrated Thermopile Sensors, Sensors and Actuators, A21–A23 (1989) 621–630.

What is claimed is:

1. A thermopile sensor for measuring differential temperatures between an external object to be measured contacting the sensing edge and a reference object contacting the reference edge of the thermopile sensor, comprising:
    a) a base layer, comprising:
        i) a reference heat sink;
        ii) a sensing heat sink; and
        iii) an etched area separating said reference and said sensing heat sinks;
    b) an electrically insulating layer on said base layer and spanning said etched area;
    c) a plurality of alternating p-type and n-type thermopile arms formed in an electrically conducting layer on said electrically insulating layer and spanning said etched area, wherein said alternating p-type and n-type thermopile arms have an electrical connection between each alternating pair of said p-type and n-type thermopile arms;
    d) a thermal reference area at an outside edge of said reference heat sink; and
    e) a thermal sensing area at an outside edge of said sensing heat sink.

2. A thermopile sensor according to claim 1, wherein said p-type thermopile arms contain boron dopant.

3. A thermopile sensor according to claim 1, wherein said n-type thermopile arms contain phosphorus dopant.

4. A thermopile sensor for measuring differential temperatures between an external object to be measured contacting the sensing edge and a reference object contacting the reference edge of the thermopile sensor, comprising:
    a) a base layer, comprising:
        i) a reference heat sink;
        ii) a sensing heat sink; and
        iii) an etched area separating said reference and said sensing heat sinks;
    b) an electrically insulating layer on said base layer and spanning said etched area;
    c) a pair of p-type and n-type thermopile arms formed in an electrically conducting layer on said electrically insulating layer and spanning said etched area, wherein said pair of p-type and n-type thermopile arms have an electrical connection between said p-type and n-type thermopile arms;
    d) a thermal reference area at an outside edge of said reference heat sink; and
    e) a thermal sensing area at an outside edge of said sensing heat sink.

5. A thermopile sensor according to claim 4, wherein said p-type thermopile arm contain boron dopant.

6. A thermopile sensor according to claim 4, wherein said n-type thermopile arm contain phosphorus dopant.

7. A thermopile sensor for measuring differential temperatures, comprising a stacked plurality of thermopile sensors according to claim 4.

* * * * *